(12) United States Patent
Masuda et al.

(10) Patent No.: US 11,911,613 B2
(45) Date of Patent: Feb. 27, 2024

(54) ELECTRICAL STIMULATION TREATMENT DEVICE

(71) Applicant: OTSUKA TECHNO CORPORATION, Naruto (JP)

(72) Inventors: Tetsuya Masuda, Naruto (JP); Takashi Hisamoto, Naruto (JP)

(73) Assignee: OTSUKA TECHNO CORPORATION, Naruto (JP)

( * ) Notice: Subject to any disclaimer, the term of this patent is extended or adjusted under 35 U.S.C. 154(b) by 96 days.

(21) Appl. No.: 16/625,538

(22) PCT Filed: May 24, 2019

(86) PCT No.: PCT/JP2019/020755
§ 371 (c)(1),
(2) Date: Dec. 20, 2019

(87) PCT Pub. No.: WO2020/079879
PCT Pub. Date: Apr. 23, 2020

(65) Prior Publication Data
US 2021/0330971 A1 Oct. 28, 2021

(30) Foreign Application Priority Data
Oct. 16, 2018 (JP) .................. 2018-195197

(51) Int. Cl.
*A61N 1/36* (2006.01)
*A61N 1/04* (2006.01)

(52) U.S. Cl.
CPC ....... *A61N 1/36007* (2013.01); *A61N 1/0456* (2013.01); *A61N 1/36034* (2017.08)

(58) Field of Classification Search
CPC .............. A61N 1/36034; A61N 1/0456; A61N 1/36007
See application file for complete search history.

(56) References Cited

U.S. PATENT DOCUMENTS

| 5,285,781 A * | 2/1994 | Brodard ............ A61N 1/36034 607/66 |
| 7,584,001 B2 | 9/2009 | Beck et al. |

(Continued)

FOREIGN PATENT DOCUMENTS

| JP | 4-231073 A | 8/1992 |
| JP | 2010-94445 A | 4/2010 |

(Continued)

OTHER PUBLICATIONS

English translation of JP2010094445, published on Oct. 20, 2008 (Year: 2008).*

(Continued)

*Primary Examiner* — Allen Porter
*Assistant Examiner* — Adreanne A. Arnold
(74) *Attorney, Agent, or Firm* — Birch, Stewart, Kolasch & Birch, LLP

(57) ABSTRACT

An electrical stimulation treatment device includes a pair of application electrodes which are disposed at a site of the skin of a person to be treated where an electrical stimulation is to be given and which supply the electrical stimulation to the skin and a control unit which is connected electrically to the application electrodes to control a magnitude of a stimulation voltage which is supplied to the application electrodes, in which the control unit includes a calculation means for calculating a magnitude of the stimulation voltage which is to be output, depending on a first maximum stimulation voltage set for each person to be treated and an elapsed time or a stimulation frequency from the start of a stimulation session of a predetermined time, and an output means for outputting the stimulation voltage while increasing the voltage in a stepwise manner based on the calculation results of the calculation means.

4 Claims, 11 Drawing Sheets

(56) References Cited

U.S. PATENT DOCUMENTS

| | | | |
|---|---|---|---|
| 2013/0289667 A1* | 10/2013 | Wacnik | A61N 1/36171 607/2 |
| 2014/0303682 A1 | 10/2014 | Siff | |
| 2018/0056061 A1 | 3/2018 | Nishimura et al. | |

FOREIGN PATENT DOCUMENTS

| | | | |
|---|---|---|---|
| JP | 2010094445 A | * | 4/2010 |
| JP | 4839457 B2 | | 12/2011 |
| JP | 5087630 B2 | | 12/2012 |
| WO | WO 2008/052085 A1 | | 5/2008 |

OTHER PUBLICATIONS

International Search Report (PCT/ISA/210) issued in PCT/JP2019/020755, dated Jul. 16, 2019.

Written Opinion of the International Searching Authority (PCT/ISA/237) issued in PCT/JP2019/020755, dated Jul. 16, 2019.

Extended European Search Report for corresponding European Application No. 19817922.8, dated Jun. 8, 2022.

* cited by examiner

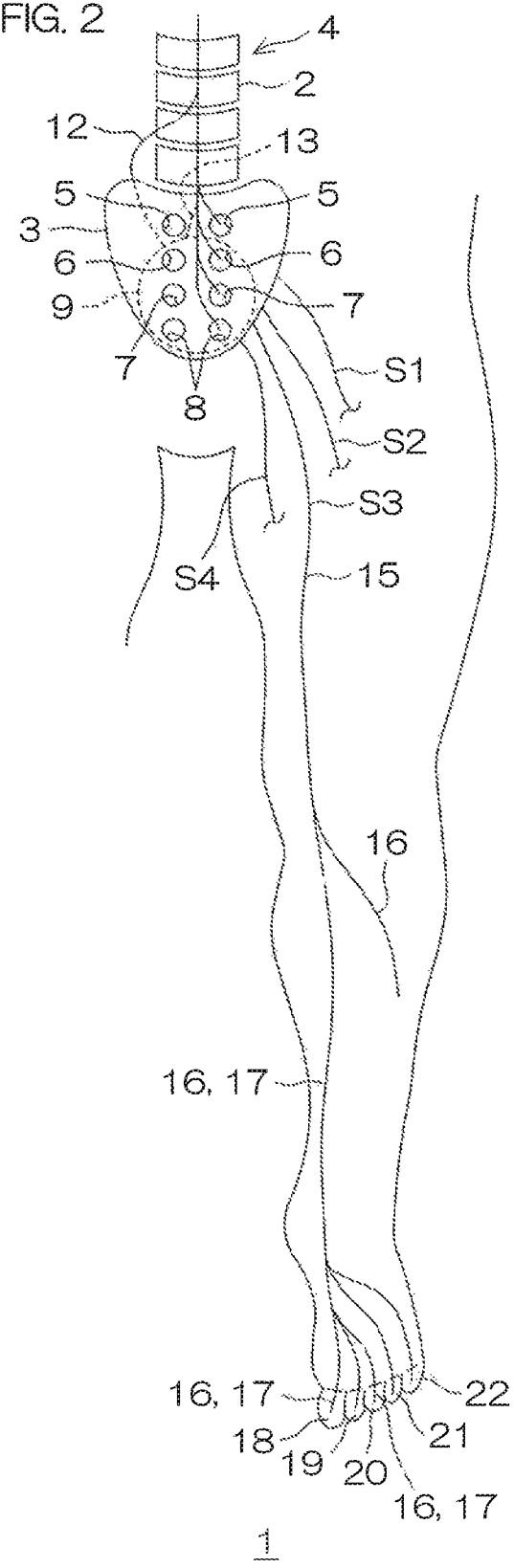

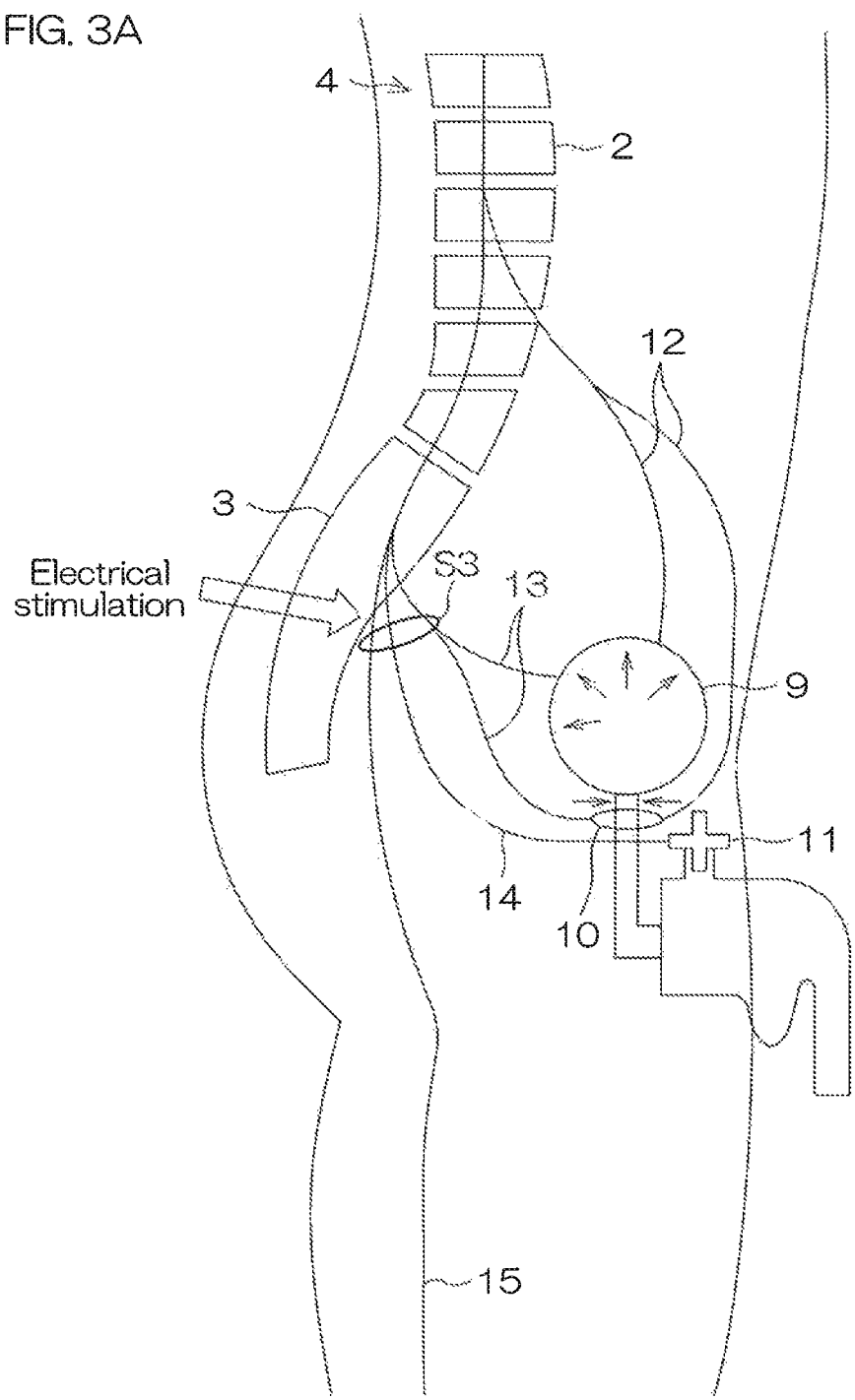

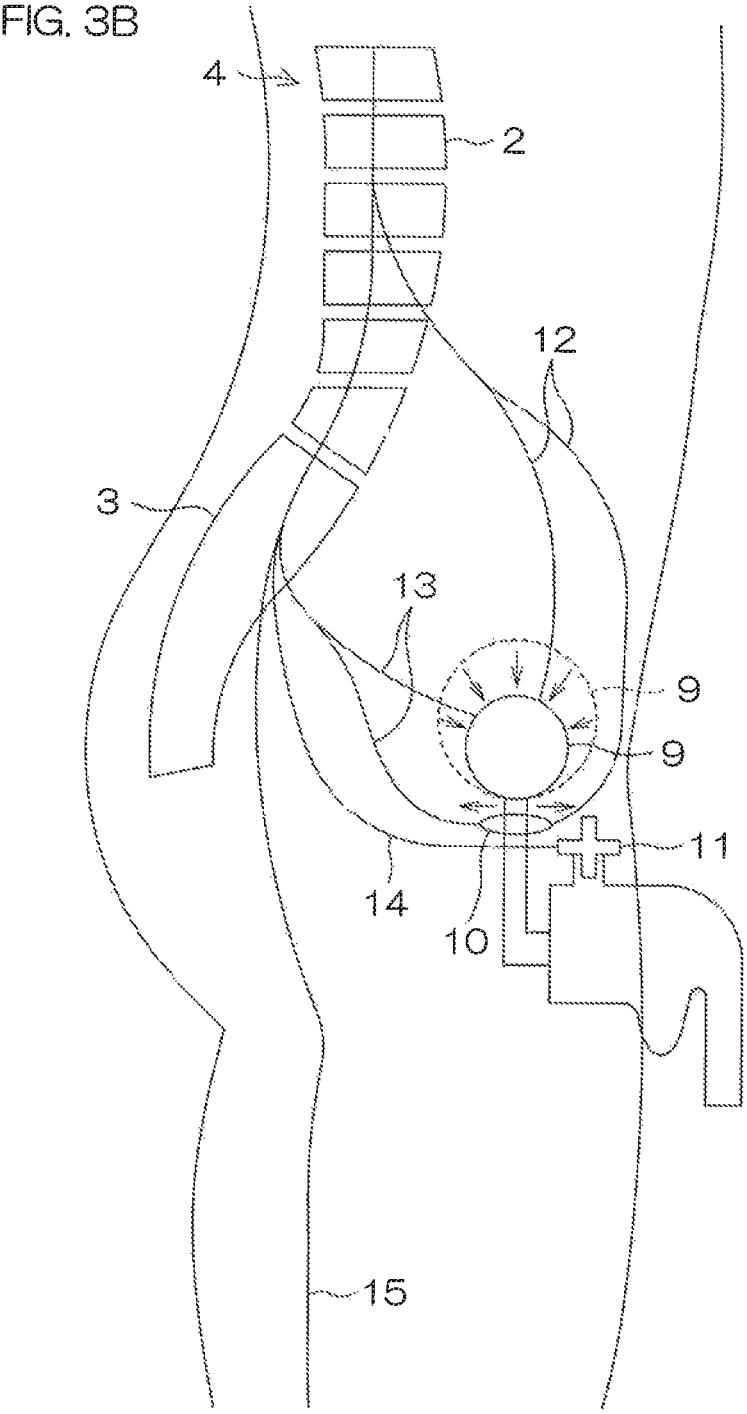

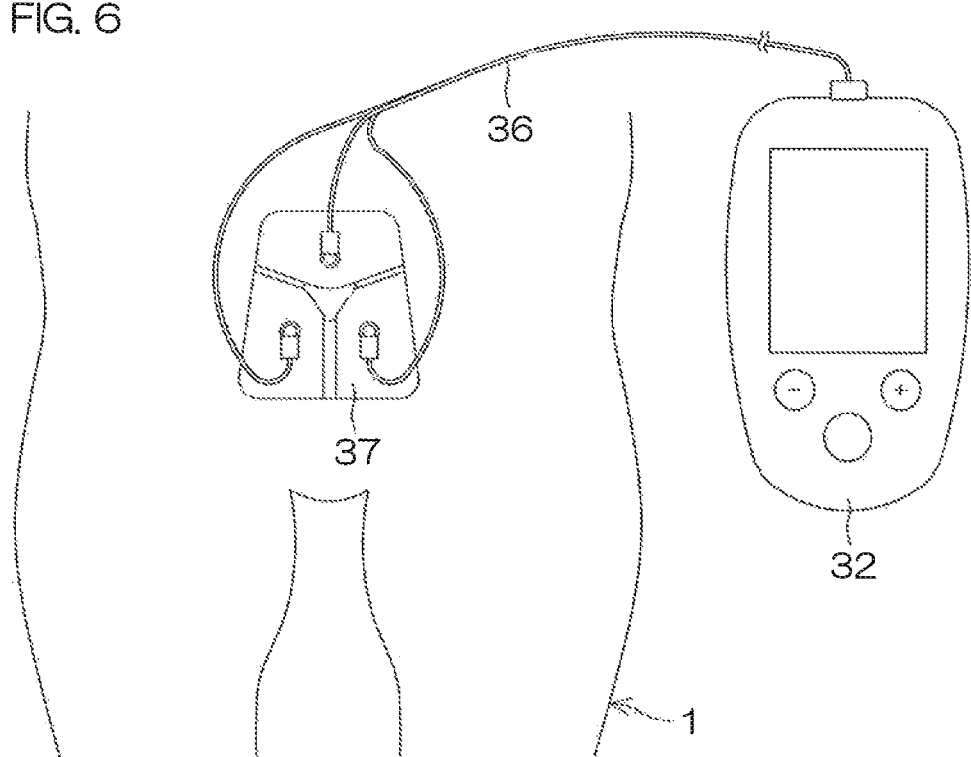

ELECTRICAL STIMULATION TREATMENT DEVICE

TECHNICAL FIELD

The present invention relates to a device which is used for electrical stimulation therapy.

BACKGROUND ART

As an example of a device used for electrical stimulation therapy, there has been so far proposed a device for treating a urination disorder.

For example, Patent Literature 1 has disclosed a pelvic viscera dysfunction or a pain treatment device which is provided with a CPU (central processing unit), an emergency stimulation switch connected to the CPU, a manual stimulation maximum value setting dial connected to the CPU, a stimulation frequency changeover switch, an output portion having a D/A converter, an electrical stimulation, and electrodes including an indifferent electrode and a different electrode (stimulation electrode) to which an electrical stimulation is applied. In this device, to the pelvic splanchnic nerve and the pudic nerve which are a second to a fourth sacral nerve of the human body, an electrical stimulation is given to excite these nerves from the skin immediately above a second to a fourth posterior sacral foramina, and a urination disorder is treated in this manner.

CITATION LIST

Patent Literature

Patent Literature 1: Japanese Patent No. 4839457

SUMMARY OF INVENTION

Technical Problem

In the electrical stimulation treatment device disclosed in Patent Literature 1, normally, a maximum stimulation voltage different for each person to be treated is set according to body shape, condition and others of a person to be treated.

However, when the device is operated at a maximum stimulation voltage from the start of stimulation, the stimulation may be too strong and give discomfort to a person to be treated.

Further, even for the same person to be treated, stimulation set in advance at a maximum stimulation voltage by a medical institution may feel strong, depending on the physical condition of the person to be treated on a particular day and the state of the skin (for example, the condition of the skin on which moisture remains due to perspiration or soon after taking a bath, etc.).

Thus, one object of the present invention is to provide an electrical stimulation treatment device which is capable of alleviating discomfort at a time of stimulation.

Further, another object of the present invention is to provide an electrical stimulation treatment device which is capable of adjusting a feeling of stimulation felt by a person to be treated himself/herself according to the condition of the skin, etc.

Solution to Problem

An electrical stimulation treatment device according to a preferred embodiment of the present invention includes a pair of application electrodes which are disposed at a site of the skin of a person to be treated where an electrical stimulation is to be given and which supply the electrical stimulation to the skin and a control unit which is connected electrically to the application electrodes to control a magnitude of a stimulation voltage supplied to the application electrodes, in which the control unit includes a calculation means for calculating a magnitude of the stimulation voltage which is to be output, depending on a first maximum stimulation voltage which is set for each person to be treated, an elapsed time or stimulation frequency from the start of a stimulation session of a predetermined time, and an output means for outputting the stimulation voltage, while increasing the voltage in a stepwise manner based on the calculation results by the calculation means.

According to this configuration, the stimulation voltage is increased in a stepwise manner from the start of the stimulation session, thus making it possible to alleviate discomfort felt by a person to be treated at a time of stimulation.

In an electrical stimulation treatment device according to a preferred embodiment of the present invention, the calculation means may include a storage portion which stores storage information based on how long a time has elapsed or how many times the stimulation has been given from the start of the stimulation session in order to attain the first maximum stimulation voltage, and may calculate an increase rate of the stimulation voltage based on the storage information of the storage portion when the elapsed time or the stimulation frequency from the start of the stimulation session is input, thereby calculating a magnitude of the stimulation voltage based on the increase rate.

An electrical stimulation treatment device according to a preferred embodiment of the present invention may include an input portion which is operated when a person to be treated feels that stimulation is strong, and the output means may not increase the stimulation voltage until termination of the stimulation session from a time when the input portion is operated, when the input portion is operated before attainment of the first maximum stimulation voltage.

According to this configuration, since an increase in the stimulation voltage is stopped from a time when a person to be treated operates the input portion, it is possible to adjust a stimulation sensation felt himself/herself by the person to be treated himself/herself according to the condition of the skin of the person to be treated (for example, a state of the skin on which moisture remains due to perspiration or soon after taking a bath, etc.).

An electrical stimulation treatment device according to a preferred embodiment of the present invention may include a switch means which is capable of switching the voltage to the first maximum stimulation voltage or a calculation stimulation voltage calculated by the calculation means as a second maximum stimulation voltage which is actually used until termination of the stimulation session, and the output means may use the calculation stimulation voltage as the second maximum stimulation voltage when the input portion is operated before attainment of the first maximum stimulation voltage.

An electrical stimulation treatment device according to a preferred embodiment of the present invention may include a comparison means for comparing information on how long a time has elapsed or how many times stimulation has been given from the start of the stimulation session in order to attain the first maximum stimulation voltage, with information on an actual elapsed time or an actual stimulation frequency from the start of the stimulation session, and a selection means for selecting a type of voltage of the switch means based on the comparison results of the comparison means when the input portion is operated.

Further, an electrical stimulation treatment device according to a preferred embodiment of the present invention may include a urination disorder treatment device.

BRIEF DESCRIPTION OF DRAWINGS

FIG. 2 is a rear view of the human body for describing innervation of urination.

FIG. 3A is a drawing for describing a mechanism of urination.

FIG. 3B is a drawing for describing a mechanism of urination.

FIG. 6 is a drawing which shows an attached state of the urination disorder treatment device.

DESCRIPTION OF EMBODIMENTS

Figure 1:
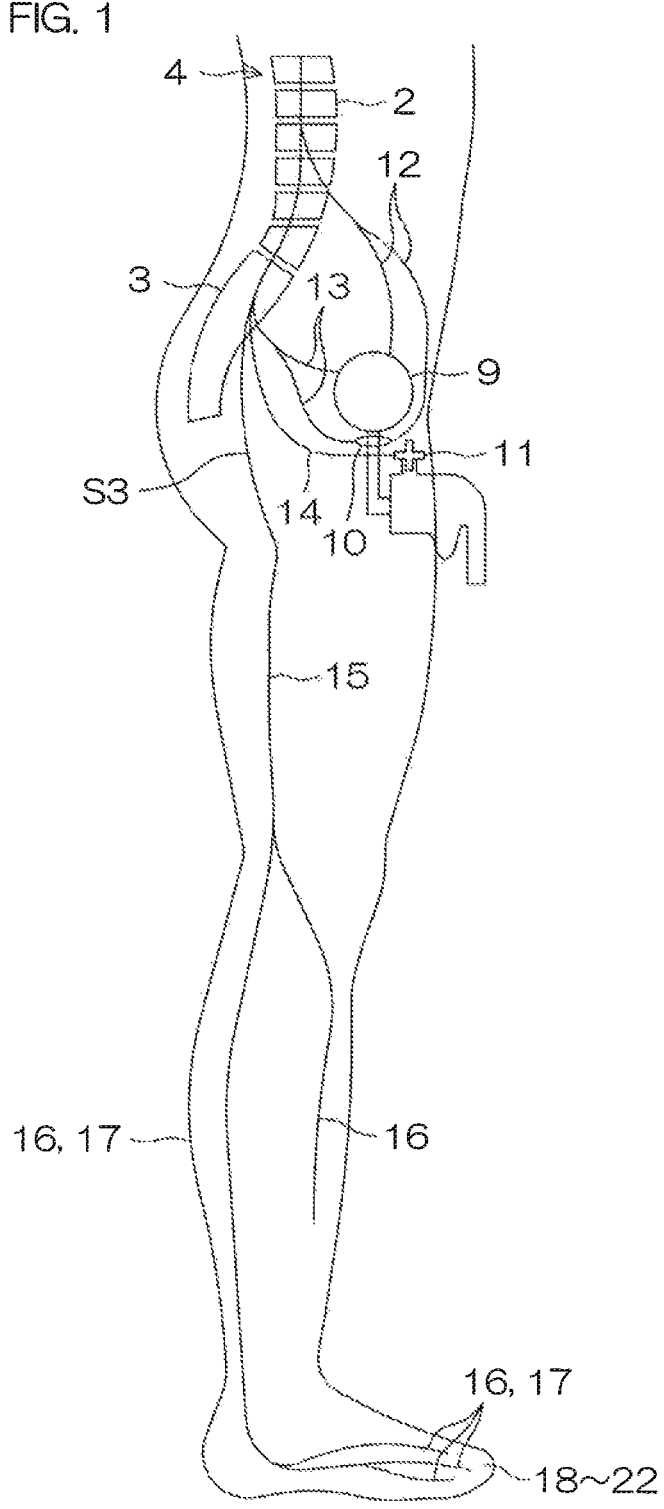
FIG. 1 is a side sectional view of the human body for describing innervation of urination.

Hereinafter, modes of executing the present invention will be described in detail with reference to attached drawings. FIG. 1 is a side sectional view of a human body 1 for describing innervation of urination. FIG. 2 is a rearview of the human body 1 which describes innervation of urination. FIG. 3A and FIG. 3B are each a drawing which describes a mechanism of urination. In FIG. 1 to FIGS. 3A and 3B, of various sites of the human body 1, there are shown only sites which are necessary for describing treatment by using a urination disorder treatment device 31 according to a preferred embodiment of the present invention, with a description of other sites being omitted here.

The human body 1 has a vertebral column 4 which includes a lumbar vertebra 2, a sacral bone 3 and others. The sacral bone 3 assumes a substantially inverted triangular shape, normally having four foramina on both sides symmetrically, from above, a first sacral foramen 5, a second sacral foramen 6, a third sacral foramen 7, and a fourth sacral foramen 8.

Further, the human body 1 has a bladder 9, an internal urethral sphincter 10 and an external urethral sphincter 11 as sites (organs and muscles) involved in collecting and discharging urine. These sites of 9 to 11 are neurologically controlled to collect and discharge urine in the human body 1.

In the human body 1, nerves mainly contributing to collection and discharge of urine are a hypogastric nerve (sympathetic nerve) 12, a pelvic nerve (parasympathetic nerve) 13 and a pudic nerve (somatic nerve) 14.

The hypogastric nerve 12 contributes to suppression of urination (urine collection) and is connected to the bladder 9 and the internal urethral sphincter 10. The pelvic nerve 13 contributes to the initiation of urination and connected to the bladder 9 and the internal urethral sphincter 10. The pudic nerve 14 is connected to the external urethral sphincter 11.

As shown in FIG. 3A, in the human body 1, first, the bladder 9 (detrusor muscle) is relaxed by a signal from the hypogastric nerve 12, by which urine can be easily collected in the bladder 9 and the internal urethral sphincter 10 is also contracted. Thereby, urine is prevented from being discharged but collected inside the bladder 9. On the other hand, as shown in FIG. 3B, the bladder 9 (detrusor muscle) is contracted by a signal from the pelvic nerve 13, and the internal urethral sphincter 10 is also relaxed. Thereby, urine is discharged outside the bladder 9. Then, the external urethral sphincter 11 as a voluntary muscle is relaxed by a command from the brain of the human body 1 (one's own volition) by way of the pudic nerve 14 which is a somatic nerve, and an abdominal muscle pressure is applied to discharge urine.

As described above, if the hypogastric nerve 12 and the pelvic nerve 13 are both normally engaged in activity to appropriately contract and relax the bladder 9 and the internal urethral sphincter 10, urine is collected or discharged normally. However, for example, when the hypogastric nerve 12 is activated at a lower level or the pelvic nerve 13 is activated excessively, the bladder 9 is more likely to contract and the internal urethral sphincter 10 is more likely to relax. As a result, urine is less easily collected in the bladder 9, which may trigger onset of a urination disorder such as a urine collection failure (overactive bladder).

Thus, in the preferred embodiment, as shown in FIG. 3A, an electrical stimulation signal is given to the skin on the sacral bone 3 from the back of the sacral bone 3, thereby stimulating the sacral plexus. More specifically, as shown in FIG. 2, there are stimulated a first sacral nerve S1 which passes through the first sacral foramen 5, a second sacral nerve S2 which passes through the second sacral foramen 6, a third sacral nerve S3 which passes through the third sacral foramen 7 and a fourth sacral nerve S4 which passes through the fourth sacral foramen 8. Thereby, for example, as shown in FIG. 3A, the third sacral nerve S3 is stimulated to suppress innervation which causes the bladder 9 to be contracted by the pelvic nerve 13. Further, this electrical stimulation is also sent to the hypogastric nerve 12, thereby accelerating innervation which allows the bladder 9 to be relaxed by the hypogastric nerve 12. As a result, suppression of the pelvic nerve 13 is well-balanced with acceleration of the hypogastric nerve 12, by which the bladder 9 is appropriately relaxed to improve an overactive bladder.

Next, the above-described electrical stimulation is also transmitted to the nerves present at sites other than the buttocks and peripheries thereof at which the sacral plexus is found. For example, as shown in FIG. 2, some of the third sacral nerves S3 partially descend the femur as an ischiadic nerve 15 and finally are divided into a peroneal nerve 16 and a tibial nerve 17. The peroneal nerve 16 and the tibial nerve 17 extend up to toes of the human body 1 (a first toe 18 (big toe), a second toe 19, a third toe 20, a fourth toe 21 and a fifth toe 22 (little toe)) as terminal portions of the ischiadic nerve 15. That is, the peroneal nerve 16 and the tibial nerve 17 of the toes 18 to 22 are connected by way of the ischiadic nerve 15 to the hypogastric nerve 12, the pelvic nerve 13 and the pudic nerve 14.

Next, a description will be given of a configuration and operation of a urination disorder treatment device 31 as an example of an electrical stimulation treatment device according to the first preferred embodiment of the present invention.

Figure 4:
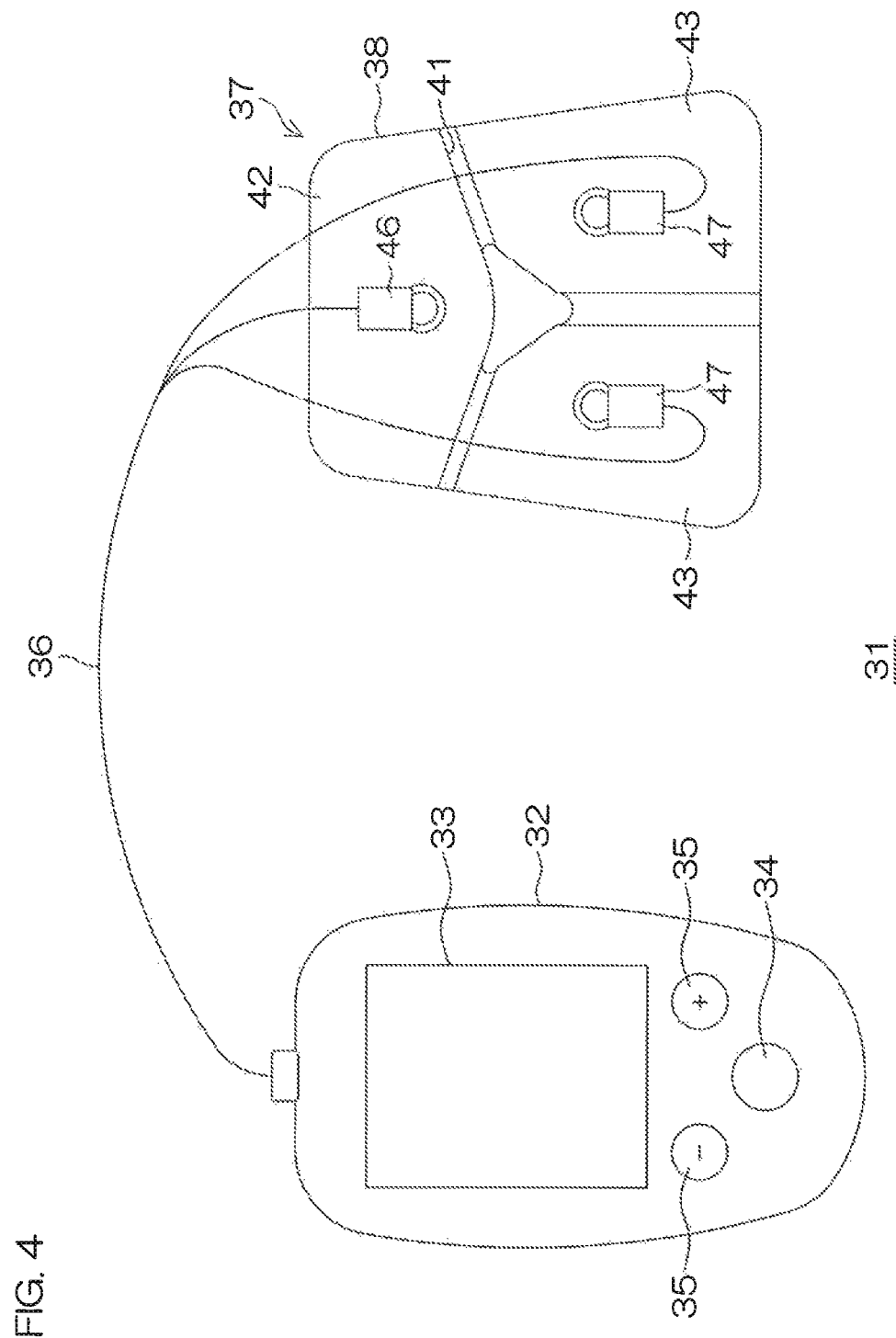
FIG. 4 is a schematic view which shows a urination disorder treatment device according to a preferred embodiment of the present invention.

FIG. 4 is a schematic view of a urination disorder treatment device 31 according to a preferred embodiment of the present invention.

The urination disorder treatment device 31 is provided as a physical configuration with a cabinet 32 (treatment device main-body), a monitor 33 installed on a front surface of the cabinet 32, a start/stop button 34 installed below the monitor 33, a plurality of operation buttons 35, 35 as an example of the input portion of the present invention, and an electrode pad 37 connected to the cabinet 32 by way of an insulation cable 36.

In this preferred embodiment, the cabinet 32 is formed in a substantially oval-shape and may be, for example, a plastic-made case. Further, although not shown in the drawing, at a back surface of the cabinet 32, there may be provided a removable back lid for housing a battery for a power source of the urination disorder treatment device 31. The power source of the urination disorder treatment device 31 may not necessarily be a battery but may be obtained, for example, from an electrical outlet by way of an AC adaptor. Alternatively, the battery may be used together with the outlet.

The monitor 33 may be formed in a rectangular shape so as to be longer along a longitudinal direction of the cabinet 32 and disposed to be closer to one end of the cabinet 32 in the longitudinal direction. Further, the monitor 33 may be, for example, a black-and-white or color liquid crystal monitor. On the monitor 33, there can be displayed, for example, a pulse waveform and a frequency of an electrical stimulation signal by the electrode pad 37, an electrocardiographic waveform and a heart rate of a person to be treated, an error message and others. Thereby, the person to be treated is able to easily know the operating state of the urination disorder treatment device 31.

The start/stop button 34 and the plurality of operation buttons 35,35 may be disposed on the other end side of the cabinet 32 in the longitudinal direction in relation to the monitor 33.

Further, the operation button 35 may have various functions depending on a type of the urination disorder treatment device 31. For example, as a memory function of the urination disorder treatment device 31, a treatment menu including a width of a pulse wave (pulse width), a frequency of a stimulation signal suitable for each of a plurality of persons to be treated is stored in the urination disorder treatment device 31, and the button, etc., that is operated in reading the treatment menu may be provided. It may also be a button which is to be depressed when a person to be treated feels that stimulation is strong in a treatment session which will be described later. The insulation cable 36 is arranged, for example, with a conducting wire covered with a protective insulation film.

Figure 5A:
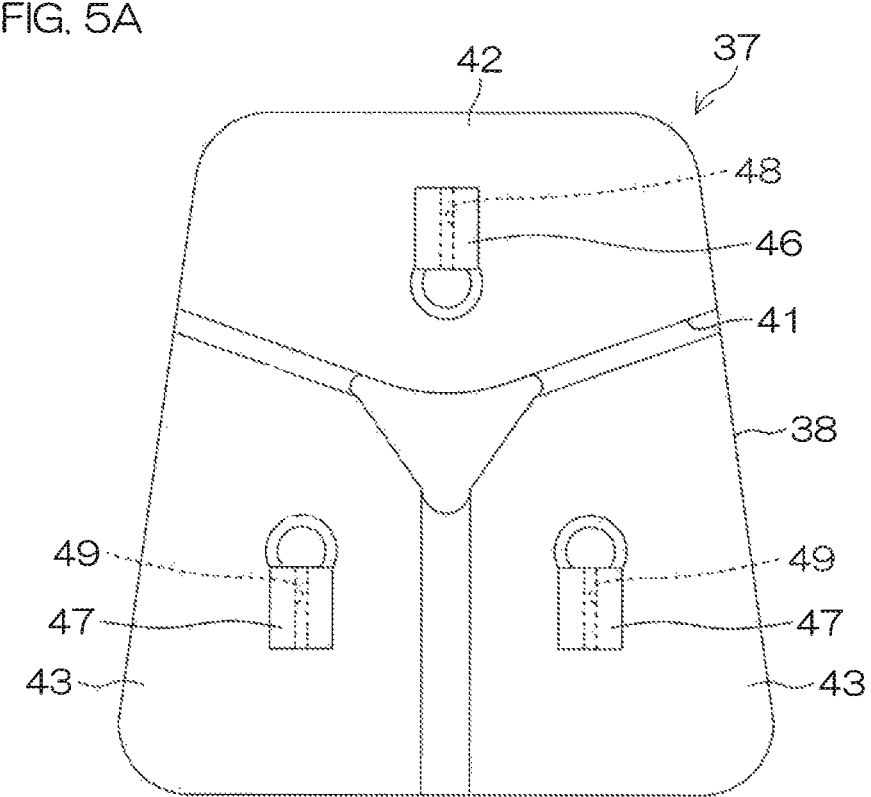
FIG. 5A and FIG. 5B are respectively a front view and a back view of an electrode pad of the urination disorder treatment device.
Figure 5B:
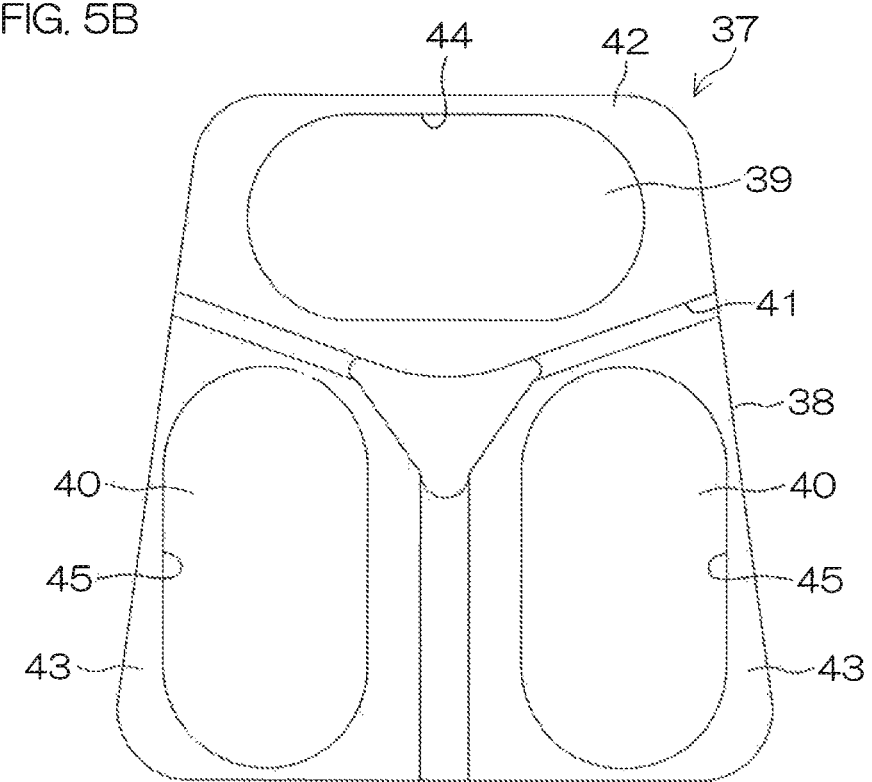

As shown in FIG. 5A and FIG. 5B, the electrode pad 37 includes a base portion 38, an indifferent electrode 39 and a pair of application electrodes 40, 40.

The base portion 38 is formed in a substantially trapezoid shape, the front surface region of which is formed into three regions 42, 43, 43 by a groove 41. More specifically, the groove 41 is formed approximately in a Y letter shape both on a front side and a back side of a base portion 38, an indifferent electrode region 42 is formed in an upper part thereof and two application electrode regions 43,43 adjacent to each other in a lateral direction are formed at a lower part thereof.

Substantially oval-shaped recessed portions 44, 45, 45 are formed respectively on the back sides of the indifferent electrode region 42 and the application electrode regions 43, 43. The indifferent electrode 39 and the pair of application electrodes 40, 40 are fitted respectively into the recessed portions 44, 45, 45 so as to be removable.

On the other hand, terminals 46, 47, 47 are installed on the front sides of the indifferent electrode region 42 and the application electrode regions 43, 43. Wiring jacks 48, 49, 49 are formed respectively inside the terminals 46, 47, 47.

In order to attach the electrode pad 37 to a human body 1, as shown in FIG. 6, a wiring plug (not shown in the drawing) connected to a leading end of the insulation cable 36 is connected to the wiring jacks 48, 49, 49, and may be adhered on the skin directly at the back of the sacral bone by way of a separately prepared jelly pad or others.

Figure 7:
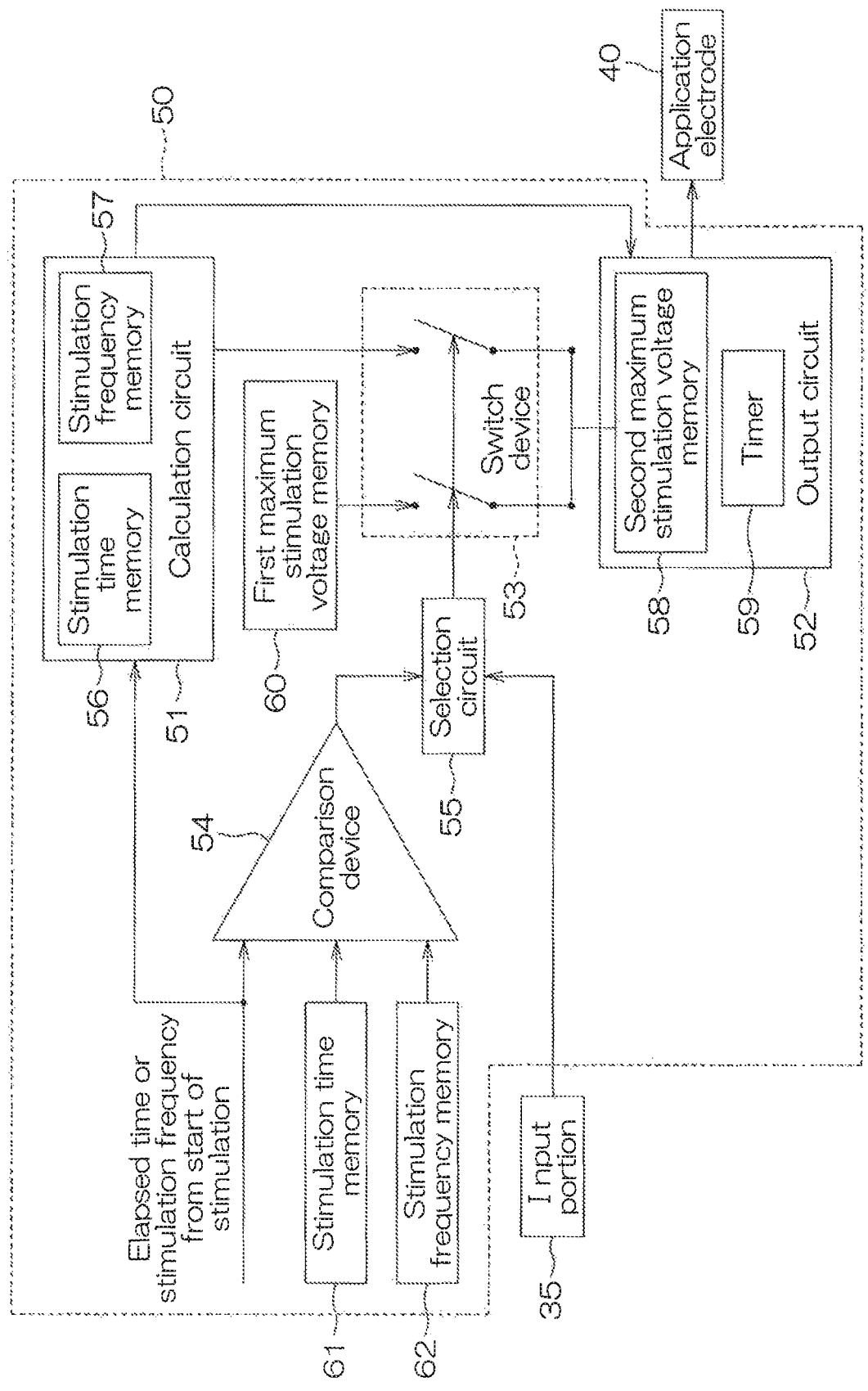
FIG. 7 is a block diagram which shows an electric configuration of the urination disorder treatment device.

FIG. 7 is a block diagram which shows an electric configuration of the urination disorder treatment device 31.

In the urination disorder treatment device 31, a circuit board (not shown in the drawing) is installed in the cabinet 32, and a controller 50 is provided on the wiring substrate as an example of the control unit of the present invention. The start/stop button 34, the operation button 35 (input portion) and the application electrodes 40 are electrically connected to the controller 50. An input signal from the start/stop button 34 or the operation button 35 is input to the controller 50, and an output signal from the controller 50 is output to the application electrodes 40.

The controller 50 may be a semiconductor chip. In this preferred embodiment, the controller 50 includes a calculation circuit 51 as an example of the calculation means of the present invention, an output circuit 52 as an example of the output means of the present invention, a switch device 53 as an example of the switch means of the present invention, a comparison device 54 as an example of the comparison means of the present invention, and a selection circuit 55 as an example of the selection means of the present invention.

The calculation circuit 51 may be a semiconductor integrated circuit (IC: Integrated Circuit) including, for example, a CPU, memories such as ROM and RAM, a timer and others.

The calculation circuit 51 is to calculate a magnitude of a stimulation voltage which is to be output depending on an elapsed time or a stimulation frequency from the start of a stimulation session (stimulation treatment). The calculation circuit 51 is provided with memories 56, 57 as an example of the storage portion of the present invention which store storage information based on how long a time has elapsed or how many times stimulation has been given from the start of the stimulation session in order to attain a maximum stimulation voltage (first maximum stimulation voltage) set by a medical institution. The first maximum stimulation voltage is set individually by a medical institution according to body shape, condition and others of a person to be treated.

In this preferred embodiment, in order to alleviate discomfort felt by a person to be treated at a time of stimulation, a stimulation voltage applied by the application electrodes 40 is to be increased in a stepwise manner. Therefore, a certain time or a certain stimulation frequency is needed before the stimulation voltage attains a first maximum stimulation voltage. For example, if such a condition is set that one minute is needed before attainment of the first maximum stimulation voltage, the stimulation voltage is increased in a stepwise manner and attains the first maximum stimulation voltage in one minute from the start of stimulation. Further, for example, if such a condition is set that stimulation is required to be given ten times before attainment of the first maximum stimulation voltage, the stimulation voltage is increased in a stepwise manner and attains the first maximum stimulation voltage after 10 times from the start of the stimulation.

Then, the memories 56, 57 are respectively a stimulation time memory 56 which stores storage information based on how long a time has elapsed from the start of a stimulation session in order to attain the first maximum stimulation voltage, and a stimulation frequency memory 57 which stores storage information based on how many times stimulation has been given from the start of the stimulation session in order to attain the first maximum stimulation voltage.

The output circuit 52 may be, for example, a semiconductor integrated circuit (IC: Integrated Circuit) including a CPU, memories such as ROM and RAM, a timer and others.

The output circuit 52 is to output a stimulation voltage calculated by the calculation circuit 51 to the application electrode 40. A second maximum stimulation voltage memory 58 and a timer 59 are installed on the output circuit 52.

Here, simply speaking, the second maximum stimulation voltage is a maximum stimulation voltage which is actually used until termination of the stimulation session. As described previously, the first maximum stimulation voltage is individually set at the urination disorder treatment device 31 by a medical institution, according to body shape, condition and others of a person to be treated. However, even the same person to be treated may feel that stimulation at the first maximum stimulation voltage set in advance by a medical institution is strong, depending on the physical condition of the person to be treated on a particular day, the condition of the skin (for example, a condition that moisture remains on the skin due to perspiration or soon after taking a bath, etc.).

Thus, in this preferred embodiment, when a person to be treated depresses the operation button 35 during a treatment session, increase in the stimulation voltage is stopped from a time when the person to be treated depresses the operation button 35, and a stimulation voltage in this stage is used as the second maximum stimulation voltage until termination of the treatment session. This second maximum stimulation voltage is equal in magnitude to the first maximum stimulation voltage or smaller than the first maximum stimulation voltage. The selection is decided by an input signal from the switch device 53 to the second maximum stimulation voltage memory 58.

Further, the timer 59 is to measure a time from the start of a treatment session to the termination thereof. When the timer 59 detects the elapse of a treatment time set in advance by a medical institution, an output from the output circuit 52 is terminated.

The switch device 53 may be, for example, a known switching element such as a semiconductor switch (MOSFET, etc.) which is turned on by application of a gate voltage or a semiconductor relay. The switch device 53 is to switch the use of the voltage to a first maximum stimulation voltage or a voltage input from the calculation circuit 51, as a second maximum stimulation voltage actually used until termination of a stimulation session. A first maximum stimulation voltage memory 60 which stores the first maximum stimulation voltage is electrically connected to the switch device 53.

The comparison device 54 may be, for example, a known comparison device, for example, an operational amplifier, a comparator and others. The comparison device 54 compares an input signal from the stimulation time memory 61 or the stimulation frequency memory 62 with an input signal of an actual elapsed time or an actual stimulation frequency from start of a stimulation session, thereby comparing whether a stimulation voltage is being increased or increase in the stimulation voltage has been terminated (that is, whether the voltage has attained a first maximum stimulation voltage). Comparison results of the comparison device 54 are output to the selection circuit 55 as an output signal. The same information as that of the stimulation time memory 56 and that of the stimulation frequency memory 57 is stored respectively in the stimulation time memory 61 and the stimulation frequency memory 62.

The selection circuit 55 may be, for example, a semiconductor integrated circuit (IC: Integrated Circuit) including a CPU, memories such as ROM and RAM, a timer and others. When the operation button 35 is depressed by a person to be treated, the selection circuit 55 outputs a control signal to the switch device 53 based on the comparison results of the comparison device 54 to select a type of voltage in the switch device 53.

Figure 8:
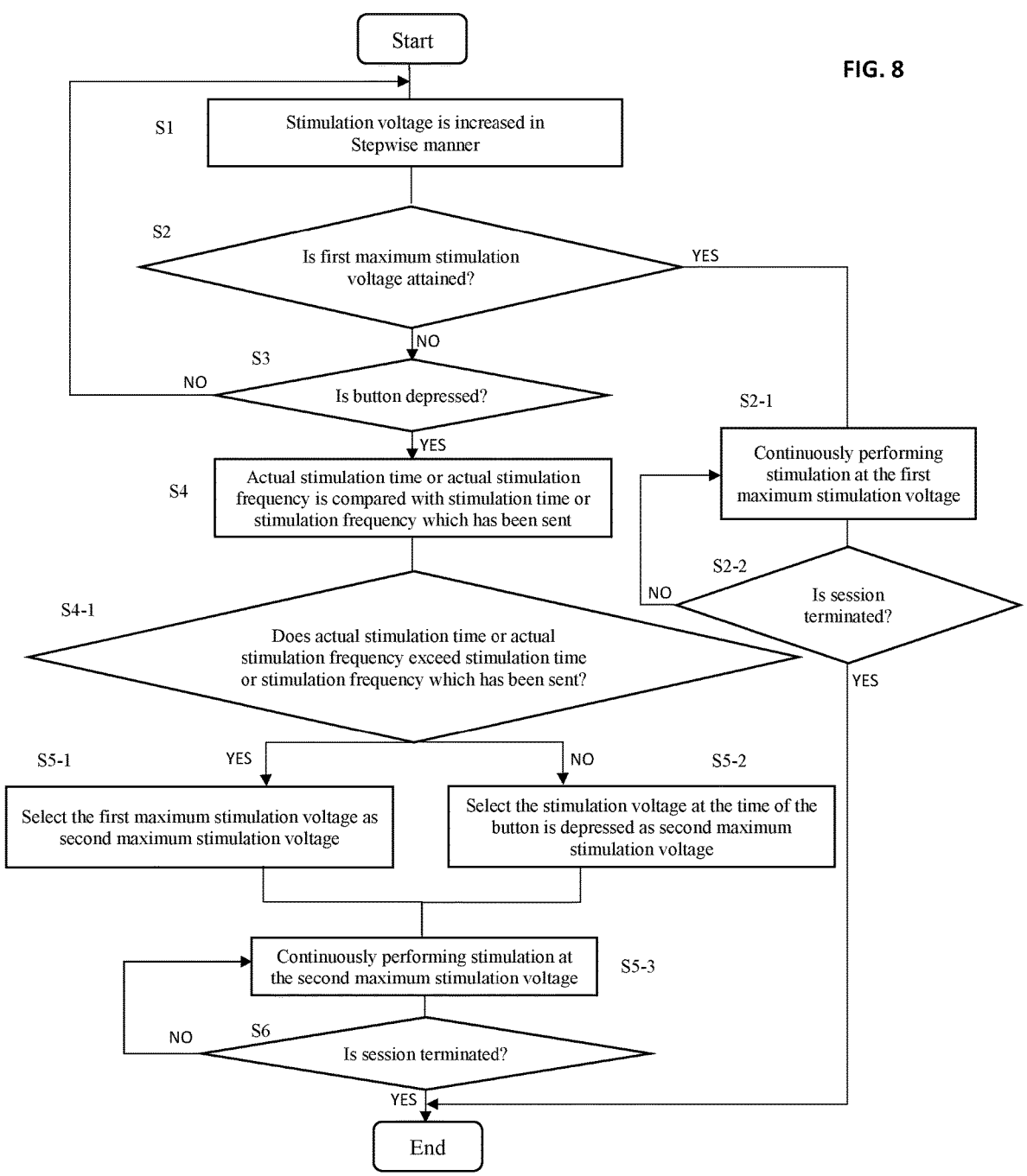
FIG. 8 is a flowchart which shows a treatment session of the urination disorder treatment device.
Figure 9:
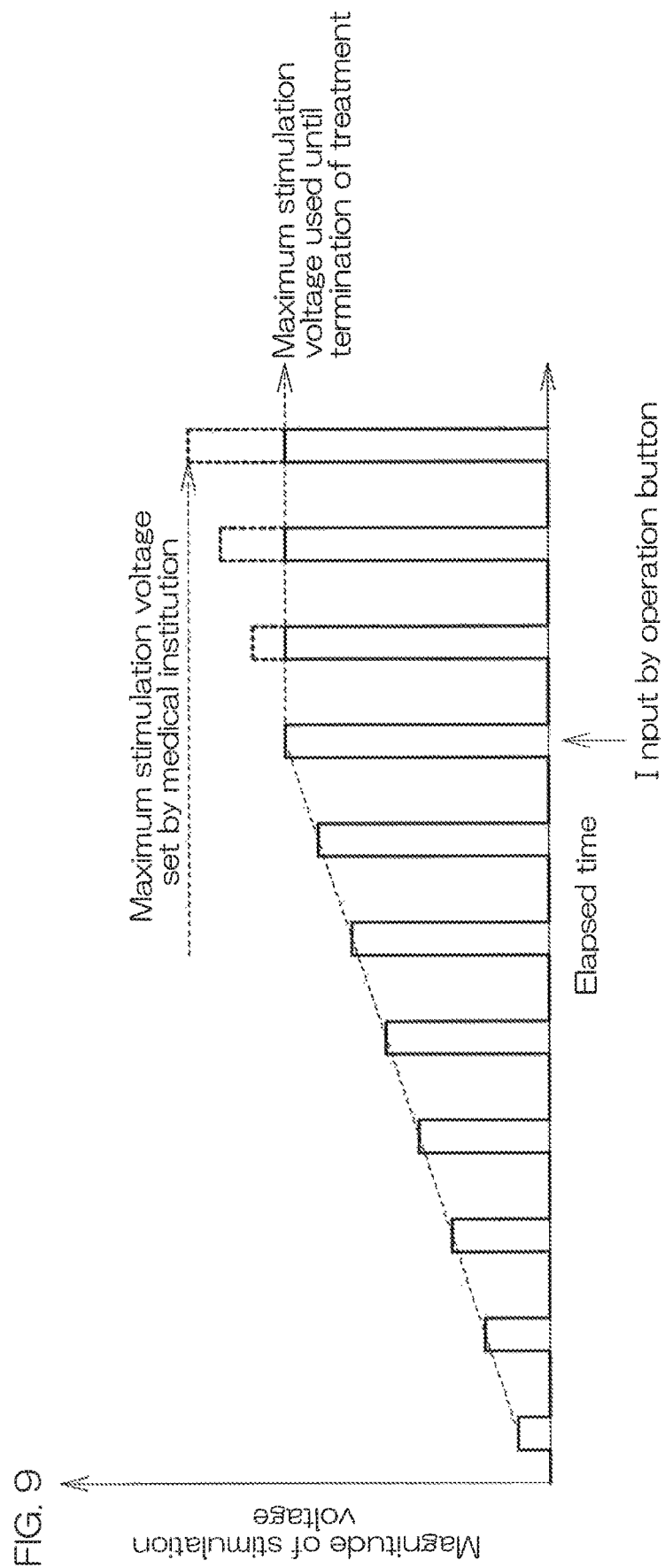
FIG. 9 is a drawing which shows a change with elapse of time in magnitude of a stimulation voltage during the treatment session.

FIG. 8 is a flowchart which shows a treatment session of the urination disorder treatment device 31. FIG. 9 is a drawing which shows a change in magnitude of a stimulation voltage with the elapse of time during a treatment session.

When being treated by using the urination disorder treatment device 31, a person to be treated first attaches, for example, the electrode pad 37 to his/her body.

After attachment of the electrode pad 37, the person to be treated operates the operation button 35, selects a treatment menu suitable for the person to be treated himself/herself and depresses the start/stop button 34. Thereby, an electrical stimulation signal is output from the electrode pad 37 to stimulate the third sacral nerve S3, thus making it possible to start treatment by the urination disorder treatment device 31. Conditions of the stimulation signal (output pulse) may be, for example, a pulse width of fps (second) to 500 μs (second) and a pulse frequency of 1 Hz to 50 Hz.

In this preferred embodiment, as shown in FIG. 9, a stimulation voltage applied by the application electrodes 40 from the start of a stimulation session is increased in a stepwise manner (Step S1). More specifically, when an input signal of an actual elapsed time or an actual stimulation frequency from the start of the stimulation session is input to the calculation circuit 51, an increase rate of the stimulation voltage is calculated based on the storage information of the stimulation time memory 56 or the stimulation frequency memory 57 and a magnitude of the stimulation voltage is calculated based on the increase rate. That is, when a certain stimulation voltage is calculated, a determination is made as to whether the stimulation voltage concerned is a stimulation voltage for which how long a time has elapsed, or the stimulation voltage concerned is a stimulation voltage for which how many times stimulation has been given from the start of the stimulation session, thereby calculating an increase rate from a previous stimulation voltage of the stimulation voltage concerned. Then, the calculation result thereof is output to the output circuit 52, and a suitable stimulation voltage is output from the output circuit 52 to the application electrodes 40.

While a stimulation voltage is being increased, a determination is made as to whether the stimulation voltage has attained a first maximum stimulation voltage (Step S2).

Here, when the voltage has attained the first maximum stimulation voltage (YES in Step S2), thereafter, stimulation is given continuously at the first maximum stimulation voltage until termination of the treatment session (Step S2-1). Then, treatment is terminated upon termination of the session (YES in Step S2-2).

On the other hand, when the stimulation voltage does not attain the first maximum stimulation voltage (NO in Step S2) or no such input is performed that stimulation is strong from the operation button 35 (NO in Step S3), the stimulation voltage is increased continuously until attainment of the first maximum stimulation voltage or until input is performed from the operation button 35.

Then, when a person to be treated feels that a stimulation voltage is strong during increase in the stimulation voltage and depresses the operation button 35 (YES in Step S3), the selection circuit 55 selects a type of voltage of the switch device 53 from comparison results input from the comparison device 54 to the selection circuit 55 (Steps S4, S4-1, S5-1 and S5-2).

For example, if an actual stimulation time or an actual stimulation frequency exceeds a time or a frequency set by the stimulation time memory 61 or the stimulation frequency memory 62 with reference to the comparison results input from the comparison device 54 to the selection circuit 55 (that is, stimulation is given for a sufficient time and at a sufficient frequency in order for the voltage to attain the first maximum stimulation voltage) (YES in Step S4-1), information of the first maximum stimulation voltage memory 60 is stored in the second maximum stimulation voltage memory 58. Thereafter, stimulation at the first maximum stimulation voltage is given continuously until termination of a treatment session (Steps S5-1 and S5-3). Then, upon termination of the session (YES in Step S6), treatment is terminated.

On the other hand, if an actual stimulation time or an actual stimulation frequency is lower than a time or a frequency set by the stimulation time memory 61 or the stimulation frequency memory 62 with reference to the comparison results input from the comparison device 54 to the selection circuit 55 (that is, no stimulation is given for such a time or at such a frequency that the voltage can attain the first maximum stimulation voltage) (NO in Step S4-1), information on the stimulation voltage at a time when the operation button 35 has been depressed is stored in the second maximum stimulation voltage memory 58 from the calculation circuit 51 (Steps S5-2 and S5-3). Thereafter, as shown in FIG. 9, stimulation is given continuously at the second maximum stimulation voltage smaller than the first maximum stimulation voltage until termination of the treatment session. Upon termination of the session (YES in Step S6), treatment is terminated.

As described so far, according to the urination disorder treatment device 31, as shown in FIG. 9, the stimulation voltage is increased in a stepwise manner from the start of a stimulation session, thus making it possible to alleviate discomfort felt by a person to be treated at a time of stimulation.

Further, as shown in FIG. 9, increase in the stimulation voltage is stopped from a time when a person to be treated operates the operation button 35. Therefore, the person to be treated is able to adjust a stimulation sensation felt himself/herself according to the condition of the skin of the person to be treated (for example, a condition that moisture remains on the skin due to perspiration or soon after taking a bath, etc.).

A description has been so far given of the preferred embodiments of the present invention. However, the present invention can be carried out in other modes.

Figure 10:
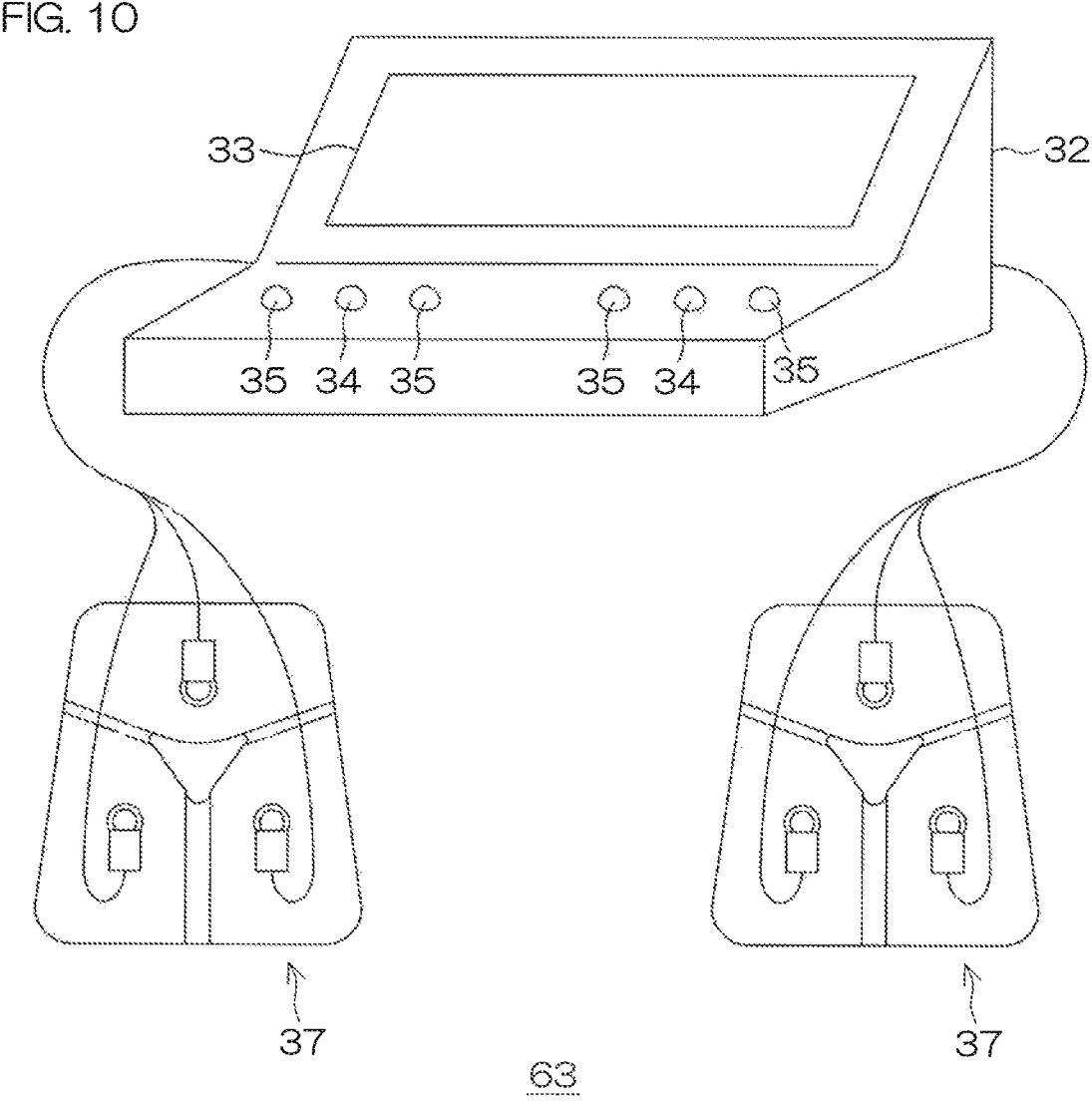
FIG. 10 is a schematic view of a urination disorder treatment device according to the other embodiment of the present invention.

For example, in the previously described preferred embodiment, a description has been given of a configuration of the portable-type urination disorder treatment device 31. As described in FIG. 10, an electric configuration of the urination disorder treatment device and control thereof may be applied to a stationary type (installation type) urination disorder treatment device 63. The above-described stationary-type urination disorder treatment device 63 is commonly used by a plurality of patients in a medical institution. Therefore, it may be provided with a memory which stores past treatment data of each patient.

Further, in the previously described embodiment, there is shown the monitor 33 for displaying a message and an image to a user. A means for displaying an operating state of the urination disorder treatment device 31 may not necessarily be the monitor 33. For example, matters which are sent to a person to be treated (for example, an error message, a wrong position of an attached electrode, etc.) are printed in advance on a front panel of the cabinet 32 and text thereof may be lit by using an LED, etc., or a lamp near the text thereof may be lit, by which the person to be treated may be notified of the matters.

Further, in the previously described preferred embodiment, only the urination disorder treatment device 31 is adopted as an example of the electrical stimulation treatment device. However, the present invention is not limited to the urination disorder treatment device but can be applied to devices in general which are used in electrical stimulation therapy for diseases other than a urination disorder.

For example, the present invention can be applied to improvement in defecation disorder. In this case, as with the previously described preferred embodiment, an electrical stimulation is given to the sacral plexus and the pudic nerve, by which nerve control which allows the anal sphincter to contract is suppressed and also nerve control which alleviates the anal sphincter is facilitated. Thereby, the anal sphincter is allowed to contract or alleviated in a well-balanced manner, and the anal sphincter is appropriately relaxed to improve a defecation disorder.

Further, although, for example, unlike the previously described embodiment, no electrical stimulation is given to the sacral plexus, the present invention can be applied to an electrical stimulation treatment device for improving dysphagia.

Further, with regard to action mechanisms of a urination disorder and a defecation disorder, in addition to action of an electrical stimulation on the sacral plexus, the pelvic floor muscle is allowed to contract, thus making it possible to improve a urination disorder and a defecation disorder (in particular, stress urinary incontinence and passive fecal incontinence).

In addition, the design of the present invention may be modified in various ways without departing from the scope described in the claims.

The present application corresponds to Japanese Patent Application No. 2018-195197 filed in the Japan Patent Office on Oct. 16, 2018, and the entire disclosure of this application is incorporated herein by reference.

REFERENCE SIGNS LIST

1: Human body
2: Vertebral column
3: Sacral bone

4: Lumbar vertebra
5: First sacral foramen
6: Second sacral foramen
7: Third sacral foramen
8: Fourth sacral foramen
9: Bladder
10: Internal urethral sphincter
11: External urethral sphincter
12: Hypogastric nerve
13: Pelvic nerve
14: Pudic nerve
15: Ischiadic nerve
16: Peroneal nerve
17: Tibial nerve
18: First toe (big toe)
19: Second toe
20: Third toe
21: Fourth toe
22: Fifth toe (little toe)
23: Electrode portion
24: Pad portion
25: Stimulation electrode
26: Indifferent electrode
27: Raised portion
28: Raised portion
29: Base portion
30: Gel
31: Urination disorder treatment device
32: Cabinet
33: Monitor
34: Start/stop button
35: Operation button
36: Insulation cable
37: Electrode pad
38: Insulation cable
39: Indifferent electrode
40: Application electrode
41: Groove
42: Indifferent electrode region
43: Application electrode region
44: Recessed portion
45: Recessed portion
46: Terminal
47: Terminal
48: Wiring jack
49: Wiring jack
50: Controller
51: Calculation circuit
52: Output circuit
53: Switch device
54: Comparison device
55: Selection circuit
56: Stimulation time memory
57: Stimulation frequency memory
58: Second maximum stimulation voltage memory
59: Timer
60: First maximum stimulation voltage memory
61: Stimulation time memory
62: Stimulation frequency memory
63: Urination disorder treatment device

The invention claimed is:

1. An electrical stimulation treatment device comprising:
a pair of application electrodes configured to apply electrical stimulation to a skin of a person;
a controller configured to be electrically connected to the application electrodes to control a magnitude of a stimulation voltage supplied to the application electrodes; and
an input portion operated by the person when the person feels that the electrical stimulation is strong,
wherein the controller includes:
a first memory storing a preset first maximum stimulation voltage;
a second memory to store a second maximum stimulation voltage, wherein the second maximum stimulation voltage is less than first maximum stimulation voltage;
a calculation circuit;
an output circuit;
a storage portion, and
a comparison device,
wherein the controller is configured to:
deliver, with the output circuit, a stimulation voltage based on a preset frequency and a preset duration,
calculate, with the calculation circuit, a stepwise increase based on a magnitude of the stimulation voltage and at least one of the preset frequency or the preset duration,
apply, with the output circuit, the stepwise increase to the stimulation voltage,
determine a first or a second condition, with the comparison device, wherein the first condition is met when the stimulation voltage reaches the first maximum stimulation voltage and the second condition is met when the stimulation voltage is less than the first maximum stimulation voltage,
when the first condition is determined, continue applying, with the output circuit, the stimulation voltage,
when the second condition is determined and the input portion has not been operated, repeat the calculate, apply and determine steps,
when the second condition is determined and the input portion has been operated, compare, with the comparison device, an actual frequency or an actual duration time corresponding to a treatment time period from a start of stimulation to the operation of the input portion,
when the actual frequency or duration exceeds the preset frequency or duration, respectively, deliver, with the output circuit, the stimulation voltage set at the first maximum voltage continuously until termination of a treatment session,
when the actual frequency or duration is lower than the preset frequency or duration, respectively,
deliver, with the output circuit, the stimulation voltage set at the second maximum voltage continuously until termination of a treatment session.

2. The electrical stimulation treatment device according to claim 1, wherein
the calculation circuit is configured to calculate an increase rate of the stimulation voltage based on the stimulation time information or the stimulation frequency information of the storage portion in response to the elapsed time or the stimulation frequency from the start of the stimulation session being input, thereby calculating a magnitude of the stimulation voltage based on the increase rate.

3. The electrical stimulation treatment device according to claim 1, wherein the electrical stimulation treatment device is a urination disorder treatment device.

4. The electrical stimulation treatment device according to claim 1, wherein any voltage reduction process is not performed and the stimulation voltage is maintained constant until the end of the treatment after setting the stimulation voltage at the second maximum voltage.

\* \* \* \* \*

UNITED STATES PATENT AND TRADEMARK OFFICE
CERTIFICATE OF CORRECTION

PATENT NO. : 11,911,613 B2
APPLICATION NO. : 16/625538
DATED : February 27, 2024
INVENTOR(S) : Tetsuya Masuda et al.

Page 1 of 1

It is certified that error appears in the above-identified patent and that said Letters Patent is hereby corrected as shown below:

On the Title Page

(73) Assignee:
Please change: "OTSUKA TECHNO CORPORATION, Naruto (JP)"
To: --OTSUKA TECHNO CORPORATION, Naruto-shi, Tokushima (JP)--

Signed and Sealed this
Twenty-third Day of April, 2024

Katherine Kelly Vidal
*Director of the United States Patent and Trademark Office*